United States Patent
Arisaka

(10) Patent No.: US 7,471,093 B2
(45) Date of Patent: Dec. 30, 2008

(54) CAPACITIVE HUMIDITY SENSOR

(75) Inventor: Naoki Arisaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 161 days.

(21) Appl. No.: 11/703,639

(22) Filed: Feb. 8, 2007

(65) Prior Publication Data

US 2007/0210807 A1  Sep. 13, 2007

(30) Foreign Application Priority Data

Mar. 13, 2006 (JP) ............... 2006-068055

(51) Int. Cl.
*G01R 27/26* (2006.01)
*G01N 27/22* (2006.01)
(52) U.S. Cl. ............... 324/664; 324/689; 73/335.04
(58) Field of Classification Search ................ 324/664, 324/663, 658, 649, 600, 689; 73/335.04, 73/29.05, 29.01, 31.05; 361/286
See application file for complete search history.

(56) References Cited

U.S. PATENT DOCUMENTS

| | | | |
|---|---|---|---|
| 5,235,267 A * | 8/1993 | Schoneberg et al. ....... 324/71.5 |
| 6,580,600 B2 | 6/2003 | Toyoda et al. | |
| 6,647,782 B2 | 11/2003 | Toyoda | |
| 7,032,448 B2 | 4/2006 | Hamamoto | |
| 7,176,700 B2 * | 2/2007 | Itakura et al. ............... 324/689 |
| 7,222,531 B2 * | 5/2007 | Isogai et al. ............. 73/335.04 |
| 7,267,002 B2 * | 9/2007 | Itakura et al. ............ 73/335.03 |
| 2002/0083777 A1 * | 7/2002 | Mochida ...................... 73/818 |
| 2002/0114125 A1 | 8/2002 | Toyoda et al. | |
| 2005/0188764 A1 | 9/2005 | Itakura et al. | |
| 2006/0096370 A1 | 5/2006 | Isogai et al. | |

FOREIGN PATENT DOCUMENTS

JP   A-6-118045   4/1994

* cited by examiner

*Primary Examiner*—Diego Gutierrez
*Assistant Examiner*—Hoai-An D Nguyen
(74) *Attorney, Agent, or Firm*—Posz Law Group, PLC

(57) ABSTRACT

A capacitive humidity sensor includes a detecting portion and a reference portion. The detecting portion includes a first sensor element, and a capacitance of the first sensor element varies in accordance with humidity. The reference portion includes a second sensor element and a capacitor. The second sensor element is connected to the first sensor element in series, and a capacitance of the second sensor element varies in accordance with the humidity. The capacitor has a constant capacitance relative to a humidity variation. The first sensor element has a gradient of a capacitance variation to the humidity variation, which is different from a gradient of the second sensor element.

20 Claims, 6 Drawing Sheets

CAPACITIVE HUMIDITY SENSOR

CROSS REFERENCE TO RELATED APPLICATION

This application is based on Japanese Patent Application No. 2006-68055 filed on Mar. 13, 2006, the disclosure of which is incorporated herein by reference.

FIELD OF THE INVENTION

The present invention relates to a capacitive humidity sensor.

BACKGROUND OF THE INVENTION

U.S. Pat. No. 6,580,600 (corresponding to JP-A-2002-243690) discloses a capacitive humidity sensor 100 shown in FIG. 8A. The sensor 100 includes a detecting portion 10 and a reference portion 20, and a capacitance of the detecting portion 10 varies in accordance with humidity.

An operation principle for the capacitive humidity sensor 100 will be described with reference to FIGS. 8A and 8B. FIG. 8A is a plan view showing the capacitive humidity sensor 100, and FIG. 8B is a graph showing a relationship between a relative humidity and capacitances Cv, Cr of the detecting portion 10 and the reference portion 20.

The detecting portion 10 includes a pair of electrodes 131a, 131b on a substrate 110, and the reference portion 20 includes a pair of electrodes 132a, 132b on the same substrate 110. The electrodes 131a, 131b, 132a, 132b are shaped into teeth of a comb. A moisture-sensing film 151 is arranged on the electrodes 131a, 131b of the detecting portion 10, and a relative permittivity (dielectric constant) of the film 151 varies in accordance with humidity. In contrast, any moisture-sensing film is not arranged on the electrodes 132a, 132b of the reference portion 20. Therefore, the capacitance Cr of the reference portion 20 is approximately constant, while the capacitance Cv of the detecting portion 10 varies in accordance with humidity, as shown in FIG. 8B.

As shown in FIG. 8A, the detecting portion 10 is connected to the reference portion 20 in series. When the capacitance Cv of the detecting portion 10 is compared with the capacitance Cr of the reference portion 20, a ratio of a voltage V12 to a voltage V23 is defined as a comparison value V12/V23. The voltage V12 for the detecting portion 10 can be expressed as Formula 1, and the voltage V23 for the reference portion 20 can be expressed as Formula 2. A voltage V0 represents a sum of the voltages V12, V23.

$$V12 = V0 \cdot Cr/(Cv+Cr) \quad \text{(Formula 1)}$$

$$V23 = V0 \cdot Cv/(Cv+Cr) \quad \text{(Formula 2)}$$

A circuit (not shown), e.g., capacitance-voltage converting circuit, is arranged on the substrate 110, and calculates a relative humidity based on the comparison value V12/V23. Thus, the relative humidity can be measured.

However, a temperature dependency may be generated in a sensor output, because the moisture-sensing film 151 has a temperature dependency. That is, a temperature dependency may be generated in a sensitivity of the sensor 100, because an amount of moisture absorbed or desorbed by the film 151 is varied by a temperature. The temperature dependency of the sensor output cannot be reduced, because any moisture-sensing film is not arranged on the reference portion 20.

If the sensor 100 is disposed in a high-temperature and high-humidity condition for a long time, the electrodes 132a, 132b may deteriorate. The capacitance Cr of the reference portion 20 may fluctuate due to the deterioration. In order to reduce the deterioration, the reference portion 20 may be protected by a gel portion. However, because the dimensions of the sensor 100 are minimized, the detecting portion 10 adjacent to the reference portion 20 may also be covered with the gel portion. In this case, response performance of the detecting portion 10 may be lowered. Further, because a process for arranging the gel portion is needed, a manufacturing cost may be increased.

In contrast, U.S. Patent Application Publication 2006/0096370 A1 (corresponding to JP-A-2006-133191) discloses a capacitive humidity sensor including a first sensor element corresponding to the detecting portion 10 and a second sensor element corresponding to the reference portion 20. Moisture-sensing films are formed on the first and second sensor elements, respectively. The first sensor element has a gradient of a capacitance variation to a humidity variation, which is different from that of the second sensor element.

Thereby, a temperature dependency in a sensor output can be reduced, because the moisture-sensing film is arranged on the second sensor element, similarly to the first sensor element. Further, the sensor can be stably used in a high-temperature and high-humidity condition for a long time, because the film protects electrodes of the second sensor element. Furthermore, because the gel portion is not needed, response performance of the first sensor element can be kept better, and the manufacturing cost can be kept low.

However, a pattern (shape) of the electrodes is different between the first sensor element and the second sensor element. For example, a clearance between the electrodes is different between the first sensor element and the second sensor element. Therefore, a difference of initial capacitances of the elements may be large relative to a capacitance variation corresponding to a humidity variation from 0% RH to 100% RH. The initial capacitance represents a capacitance at a predetermined humidity, e.g., 0% RH or 100% RH. The large difference of the initial capacitances of the elements may generate noises.

SUMMARY OF THE INVENTION

In view of the foregoing and other problems, it is an object of the present disclosure to provide a capacitive humidity sensor.

According to an aspect of the disclosure, a capacitive humidity sensor includes a detecting portion and a reference portion. The detecting portion includes a first sensor element having a first moisture-sensing film. A relative permittivity of the first moisture-sensing film varies in accordance with humidity. Therefore, a first capacitance of the first sensor element varies in accordance with the humidity. The reference portion includes a second sensor element having a second moisture-sensing film, and a capacitor. The second sensor element is connected to the first sensor element in series. A relative permittivity of the second moisture-sensing film varies in accordance with the humidity such that a second capacitance of the second sensor element varies in accordance with the humidity. The capacitor is connected to the second sensor element in parallel, and a third capacitance of the capacitor is constant relative to a humidity variation. The first sensor element has a first gradient of a first capacitance variation to the humidity variation, which is different from a second gradient of a second capacitance variation to the humidity variation in the second sensor element.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF PREFERRED EMBODIMENT

First Embodiment

Figure 1A:
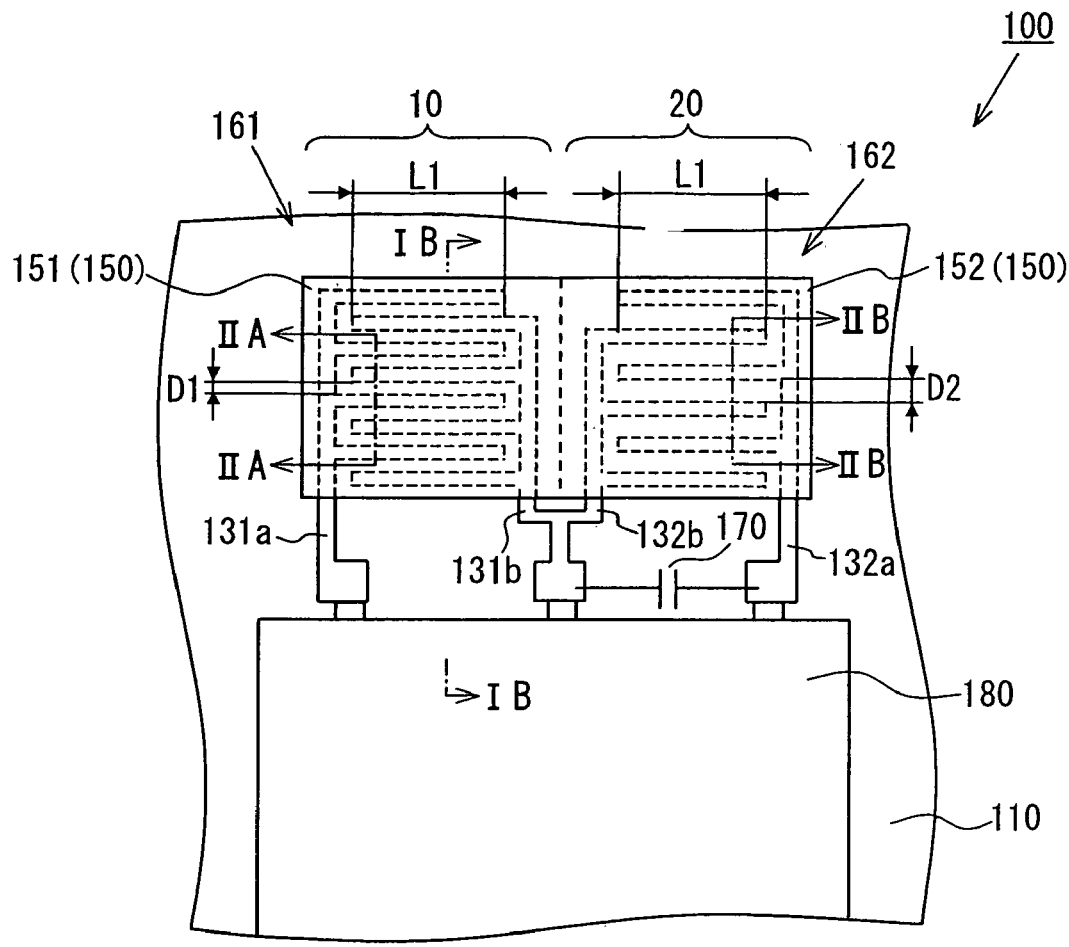
FIG. 1A is a schematic plan view showing a capacitive humidity sensor according to a first embodiment.
Figure 1B:
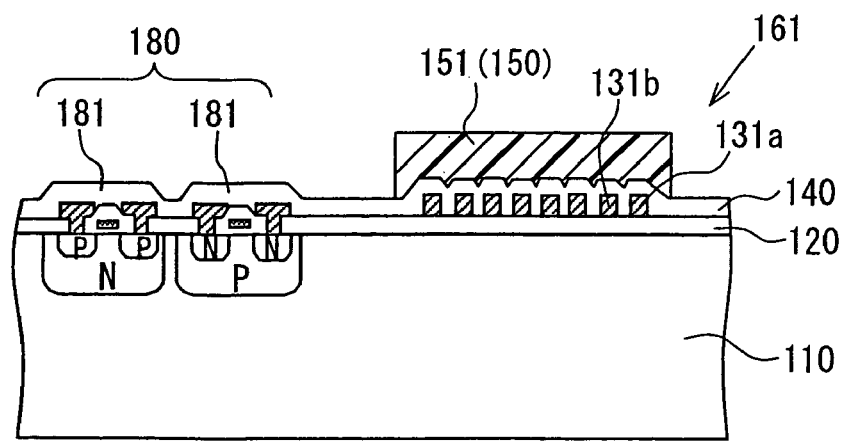
FIG. 1B is a cross-sectional view taken along line IB-IB in FIG. 1A.

As shown in FIGS. 1A and 1B, a capacitive humidity sensor 100 includes a semiconductor substrate 110 made of silicon, for example, in a first embodiment. An insulation film 120 made of oxide silicon, for example, is layered on the semiconductor substrate 110, as shown in FIG. 1B. A pair of detecting electrodes 131a, 131b is arranged on the insulation film 120, and the electrodes 131a, 131b face each other with a clearance therebetween.

A capacitance between the detecting electrodes 131a, 131b varies in accordance with humidity. Each of the detecting electrodes 131a, 131b is shaped into teeth of a comb, as shown in FIG. 1A. Due to this shape, a facing area of the detecting electrodes 131a, 131b can be increased, while an area occupied by the detecting electrodes 131a, 131b can be reduced. Thereby, sensitivity of the sensor 100 can be improved, because a variation of the capacitance can be increased. However, the shape of the detecting electrodes 131a, 131b is not limited to this.

In order to form the detecting electrodes 131a, 131b, a wiring material, e.g., aluminum, copper, gold, platinum or poly-silicon, is deposited on the insulation film 120 by evaporating or sputtering. Thereafter, a pattern of the teeth of the comb is formed by a lithography process. In the first embodiment, the detecting electrodes 131a, 131b are made of aluminum.

A pair of reference electrodes 132a, 132b is arranged on the insulation film 120 with a clearance from the detecting electrodes 131a, 131b. The reference electrodes 132a, 132b are made of the same material as the detecting electrodes 131a, 131b, and shaped into a pattern (shape) different from the detecting electrodes 131a, 131b. Specifically, as shown in FIG. 1A, an area occupied by the reference electrodes 132a, 132b is approximately equal to the area occupied by the detecting electrodes 131a, 131b. That is, outline dimensions are approximately the same between the areas. The detecting electrodes 131a, 131b face each other with a facing dimension L1 in an electrode longitudinal direction, and the reference electrodes 132a, 132b have approximately the same facing dimension L1, as shown in FIG. 1. In contrast, a clearance D1 between the detecting electrodes 131a, 131b is different from a clearance D2 between the reference electrodes 132a, 132b. Each detecting electrode 131a, 131b have four comb-teeth, while each reference electrode 132a, 132b have three comb-teeth.

Figure 2A:
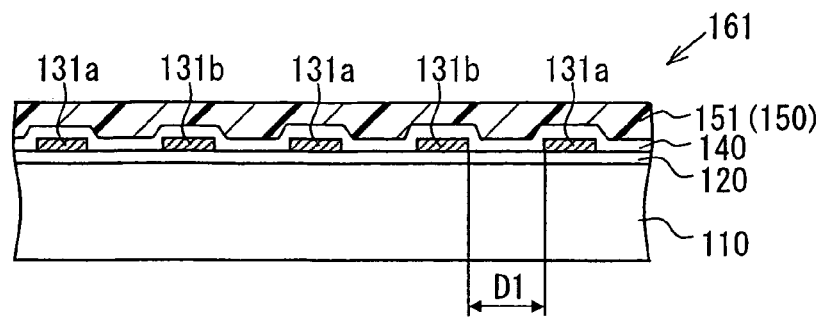
FIG. 2A is a cross-sectional view taken along line IIA-IIA in FIG. 1A.
Figure 2B:
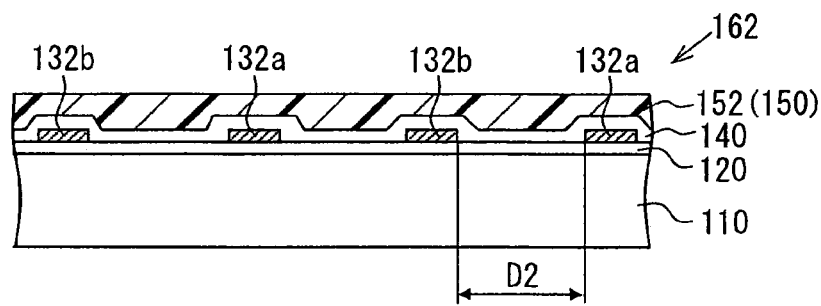
FIG. 2B is a cross-sectional view taken along line IIB-IIB in FIG. 1A.

A protection film 140 made of silicon nitride, for example, is arranged on the insulation film 120 so as to cover the detecting electrodes 131a, 131b and the reference electrodes 132a, 132b, as shown in FIGS. 2A and 2B. The protection film 140 is not drawn in FIG. 1A for convenience. The protection film 140 is deposited in a constant thickness by using a plasma chemical vapor deposition (CVD) method, for example. However, in a case where the detecting electrodes 131a, 131b and the reference electrodes 132a, 132b have sufficient corrosion resistance against water, the protection film 140 may be eliminated.

A first moisture-sensing film 151 for absorbing and desorbing moisture is arranged on the protection film 140 so as to cover the detecting electrodes 131a, 131b and a clearance between the detecting electrodes 131a, 131b. The first moisture-sensing film 151 is made of polyimide, for example. A second moisture-sensing film 152 for absorbing and desorbing moisture is arranged on the protection film 140 so as to cover the reference electrodes 132a, 132b and a clearance between the reference electrodes 132a, 132b. The second moisture-sensing film 152 is made of polyimide, for example. The first and second moisture-sensing films 151, 152 are made of the same material, and integrated into a moisture-sensing film 150. In order to form the moisture-sensing film 150, a polyimide film is disposed on the protection film 140 by a spin coat method or a printing method, and hardened by heating. The film 150 has a temperature dependency, that is, an amount of moisture absorbed or desorbed by the film 150 is varied based on a temperature. However, a temperature dependency of a sensor output can be reduced, because the first and second moisture-sensing films 151, 152 are respectively arranged on the electrodes 131a, 131b and 132a, 132b. That is, a temperature dependency in a sensitivity of the sensor 100 can be reduced.

A first sensor element 161 is constructed with the detecting electrodes 131a, 131b and the first moisture-sensing film 151. A second sensor element 162 is constructed with the reference electrodes 132a, 132b and the second moisture-sensing film 152. A gradient of a capacitance variation to a humidity variation is different between the first and second sensor elements 161, 162.

Here, because the elements 161, 162 respectively have the films 151, 152, each of the capacitances of the elements 161, 162 varies in accordance with humidity. Further, because the clearances D1, D2 are different between the elements 161, 162, and because the number of the comb-teeth is different between the elements 161, 162, the gradients of the capacitance variation to the humidity variation are different between the elements 161, 162. That is, a relationship between the capacitances of the sensor elements 161, 162 and a relative humidity is linear, and gradients of the linear curves are different between the elements 161, 162. Thus, a sensitivity difference is secured between the elements 161, 162.

However, when structures are different between the detecting electrodes 131a, 131b and the reference electrodes 132a, 132b, initial capacitances are different between the elements 161, 162 other than the gradients. The initial capacitance represents a capacitance corresponding to the relative humidity of 0% in the first embodiment. When a difference between the initial capacitances is large relative to a capacitance variation corresponding to a humidity variation from 0% RH to 100% RH, noises may be generated by the difference between the initial capacitances. The difference between the initial capacitances represents a capacitance difference at a predetermined relative humidity, e.g., 0% or 10%.

In the first embodiment, as shown in FIG. 1A, a capacitor 170 is connected to the reference electrodes 132a, 132b in parallel. That is, a reference portion 20 is constructed with the second sensor element 162 and the capacitor 170, while a detecting portion 10 is constructed with the first sensor element 161. The capacitor 170 has a constant capacitance relative to the humidity variation. The capacitor 170 is mounted to the substrate 110 through a solder (not shown) as an external electrical component.

Figure 3:
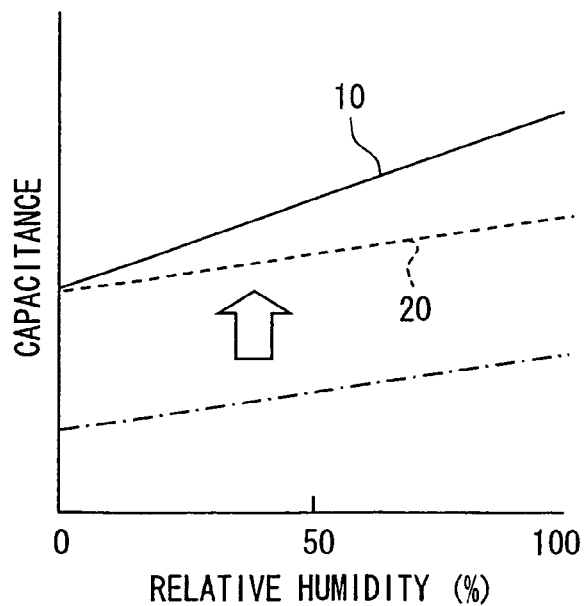
FIG. 3 is a graph showing a relationship between a relative humidity and capacitances in the sensor.

The capacitance of the capacitor 170 is set such that the difference of the initial capacitances between the detecting portion 10 and the reference portion 20 is made smaller or approximately zero. Therefore, the difference of the initial capacitances can be reduced, as shown in FIG. 3, in which a dashed line represents a relationship between a capacitance and a relative humidity in the reference portion 20, and a chained line represents a relationship between a capacitance and a relative humidity in a conventional reference portion without the capacitor 170.

Further, as shown in FIG. 1A, the detecting electrodes 131a, 131b and the reference electrodes 132a, 132b are electrically connected to a circuit 180 including a capacitance-voltage converting circuit (not shown) through a pad, i.e., external connection terminal. As shown in FIG. 1B, the circuit 180 includes CMOS transistors 181, and signals of the capacitance variations in the detecting portion 10 and the reference portion 20 are processed in the circuit 180. A description of the circuit 180 is omitted, because the circuit 180 has been described in detail, for example in JP-A-2003-28824.

According to the first embodiment, the second sensor element 162 of the reference portion 20 includes the second moisture-sensing film 152. Thus, a temperature dependency in a sensor output can be reduced. Especially, because the first and second moisture-sensing films 151, 152 are integrated into the moisture-sensing film 150 with the same material, the temperature dependency can be effectively reduced.

Further, because the second moisture-sensing film 152 is formed on the reference electrodes 132a, 132b, the sensor 100 can be stably used in a high-temperature and high-humidity environment for a long time. In addition, because the second moisture-sensing film 152 protects the reference electrodes 132a, 132b, conventional disadvantages are resolved. That is, response performance can be kept better, and manufacturing cost can be kept low.

Further, the capacitor 170 is connected to the second sensor element 162 in parallel. Thus, noises can be reduced, because the difference in the initial capacitances can be reduced between the detecting portion 10 and the reference portion 20.

Figure 4A:
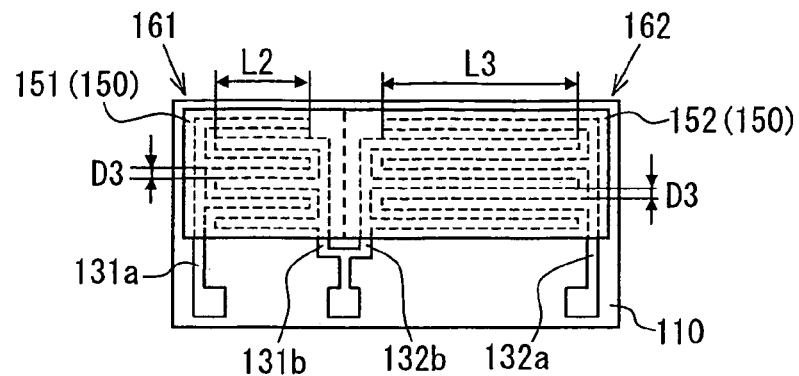
FIG. 4A is a plan view showing a modified electrodes pattern.
Figure 4B:
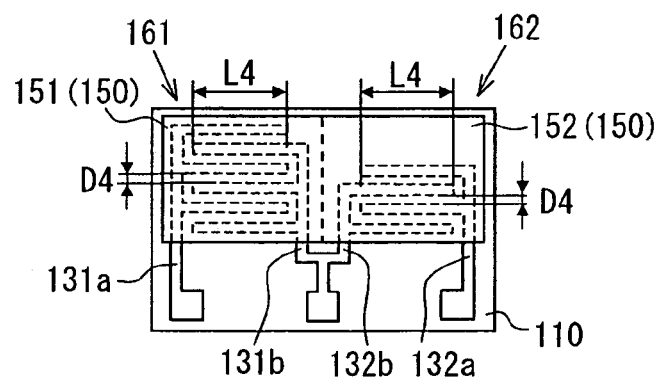
FIG. 4B is a plan view showing another modified electrodes pattern.

Further, the gradients of the capacitance variation to the humidity variation are made different between the elements 161, 162 by the different clearances D1, D2 and the different numbers of the comb-teeth. Alternatively, as shown in FIG. 4A, a facing dimension L2 between the detecting electrodes 131a, 131b and a facing dimension L3 between the reference electrodes 132a, 132b may be made different from each other. Alternatively, as shown in FIG. 4B, the number of the comb-teeth may be made different between the detecting electrodes 131a, 131b and the reference electrodes 132a, 132b. Alternatively, these alternations may be combined.

Figure 5:
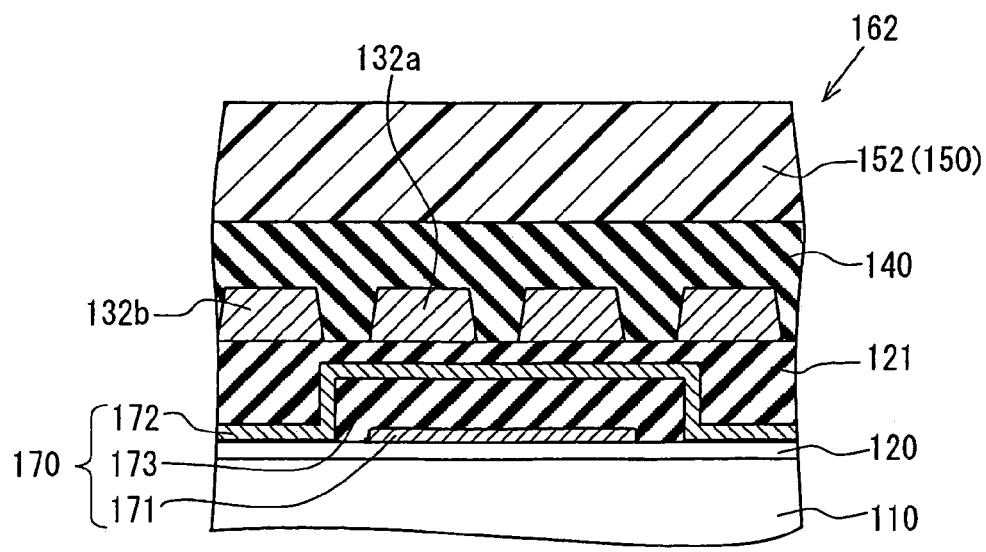
FIG. 5 is a cross-sectional view showing a modified capacitor in the sensor.

Further, the capacitor 170 is mounted to the substrate 110 through the insulation film 120 as an electrical component. Alternatively, as shown in FIG. 5, the capacitor 170 may have a stack structure, which is positioned under the second sensor element 162. That is, the capacitor 170 may be disposed between the insulation film 120 and the reference electrodes 132a, 132b. Alternatively, the stack structure may be positioned under the first sensor element 161. Because a size of the substrate 110 can be made smaller due to the stack structure, a size of the sensor 100 can be made smaller. The capacitor 170 includes facing electrodes 171, 172 and an insulating film 173 between the electrodes 171, 172. The electrodes 171, 172 are made of polysilicon, and the insulating film 173 is made of oxide silicon or nitride silicon, for example. A boron phosphorus silicate glass (BPSG) layer 121 is disposed between the reference electrodes 132a, 132b and the electrode 172 of the capacitor 170.

Further, the electrodes 131a, 131b (132a, 132b) are formed into the shape of the teeth of the comb. However, the shape of the electrodes 131a, 131b (132a, 132b) are not limited to this, as long as the electrodes 131a, 131b (132a, 132b) are arranged on the substrate 110 with a predetermined clearance therebetween.

Second Embodiment

A first moisture-sensing film 151 and a second moisture-sensing film 152 are made of different materials in a second embodiment, thereby a gradient of a capacitance variation to a humidity variation is made different between a first sensor element 161 and a second sensor element 162. Detecting electrodes 131a, 131b and reference electrodes 132a, 132b have the same construction (pattern) in the second embodiment. The other parts in the second embodiment may be made similar to the first embodiment.

Figure 6:
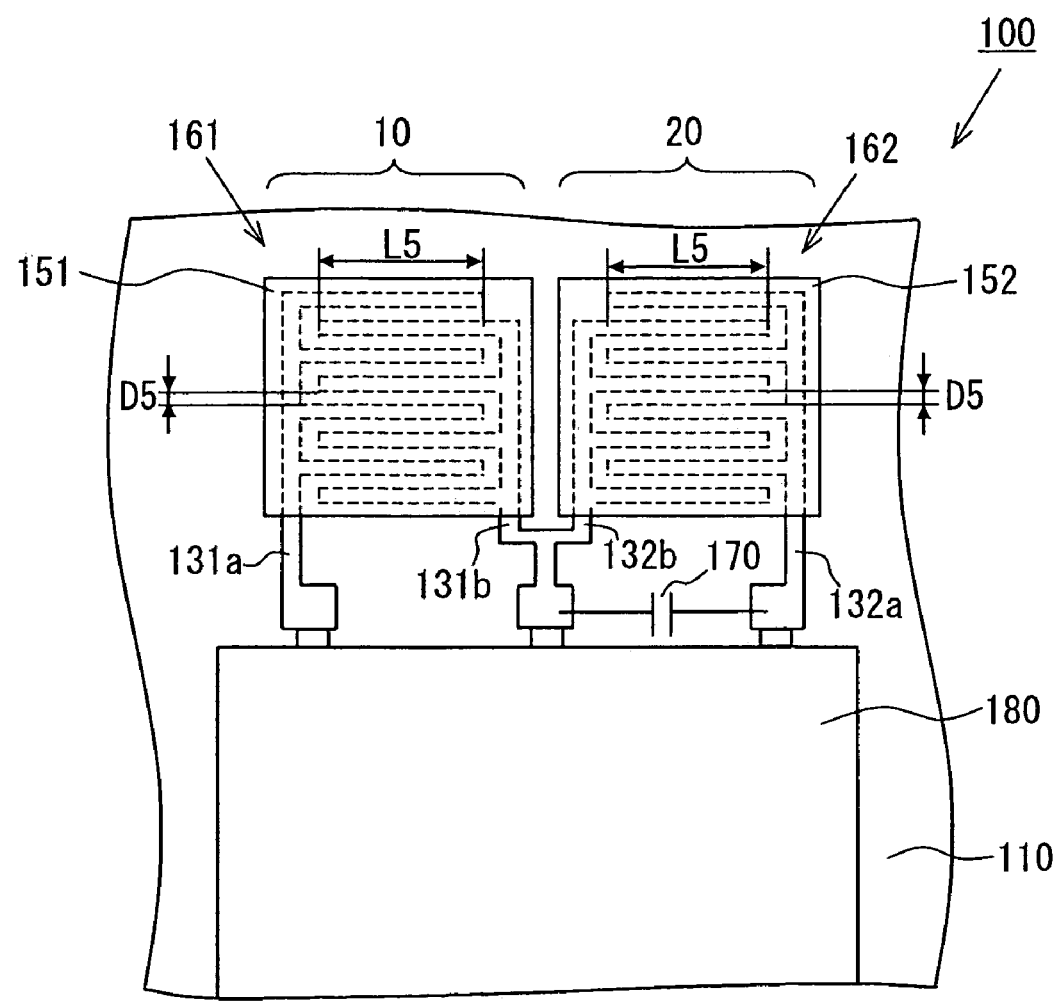
FIG. 6 is a schematic plan view showing a capacitive humidity sensor according to a second embodiment.

As shown in FIG. 6, a clearance D5 between the detecting electrodes 131a, 131b is approximately equal to a clearance D5 between the reference electrodes 132a, 132b. A facing dimension L5 between the detecting electrodes 131a, 131b is approximately equal to a facing dimension L5 between the reference electrodes 132a, 132b. The first and second sensor elements 161, 162 have the same number, e.g., eight, of electrodes, respectively. In contrast, the first moisture-sensing film 151 and the second moisture-sensing film 152 are made of different materials.

The different materials have different variations of relative permittivity relative to a predetermined humidity variation. That is, a gradient of a capacitance variation to a humidity variation is different between the first and second sensor elements 161, 162. In the second embodiment, the film 151 is made of polyimide, and the film 152 is made of polyamide-imide, for example. However, both of the films 151, 152 may be made of polyimide, as long as the variations of relative permittivity are different relative to the predetermined humidity variation.

According to the second embodiment, the second sensor element 162 of the reference portion 20 includes the second moisture-sensing film 152. Therefore, a temperature dependency in a sensor output can be reduced.

Further, because the second film 152 is formed on the reference electrodes 132a, 132b, the sensor 100 can be stably used in a high-temperature and high-humidity environment for a long time. Response performance can be kept better, and manufacturing cost can be kept low. Furthermore, noises can be reduced, because a difference of the initial capacitances between the detecting portion 10 and the reference portion 20 can be reduced due to the capacitor 170.

In the second embodiment, the detecting electrodes 131a, 131b and the reference electrodes 132a, 132b have the same construction, and the first moisture-sensing film 151 and the second moisture-sensing film 152 are made of different materials. However, the detecting electrodes 131a, 131b and the reference electrodes 132a, 132b may have different constructions, while the films 151, 152 are made of the different materials.

Third Embodiment

Figure 7A:
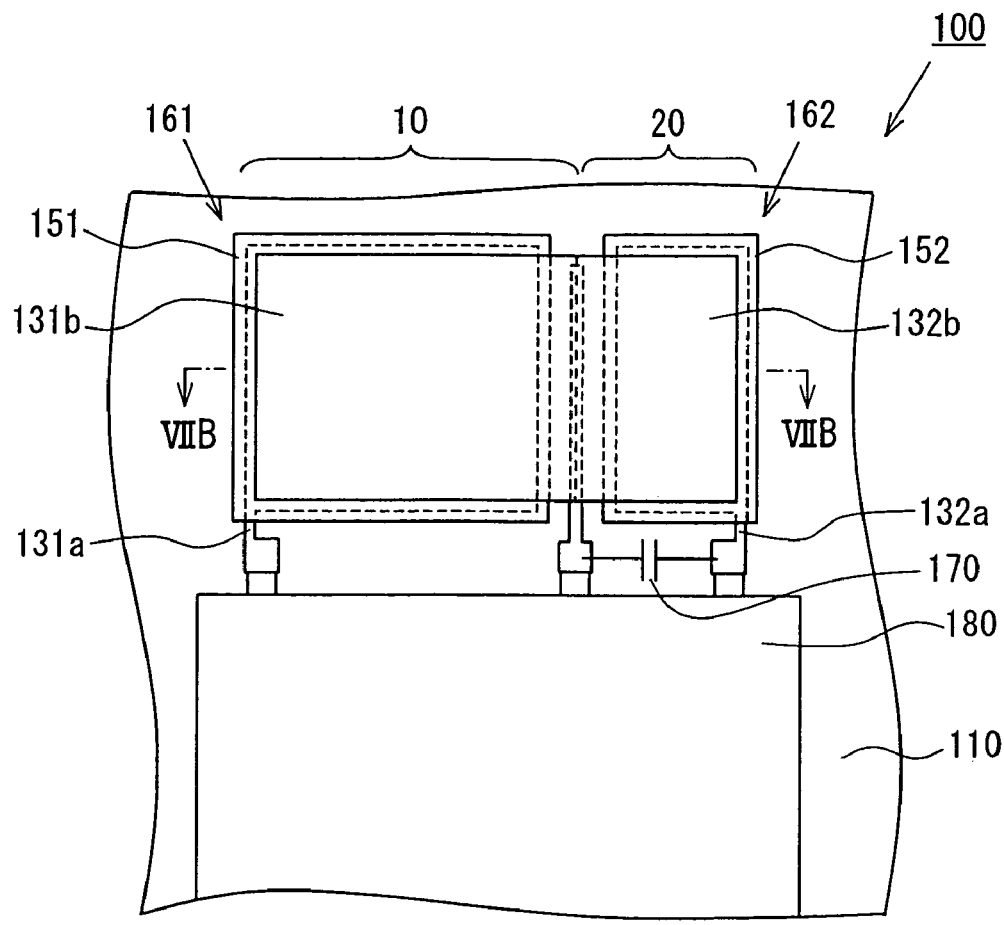
FIG. 7A is a schematic plan view showing a capacitive humidity sensor according to a third embodiment.
Figure 7B:
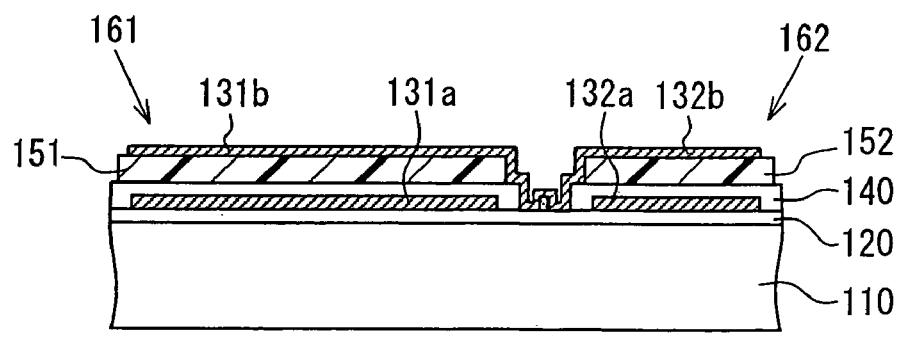
FIG. 7B is a cross-sectional view taken along line VIIB-VIIB in FIG. 7A.
Figure 8A:
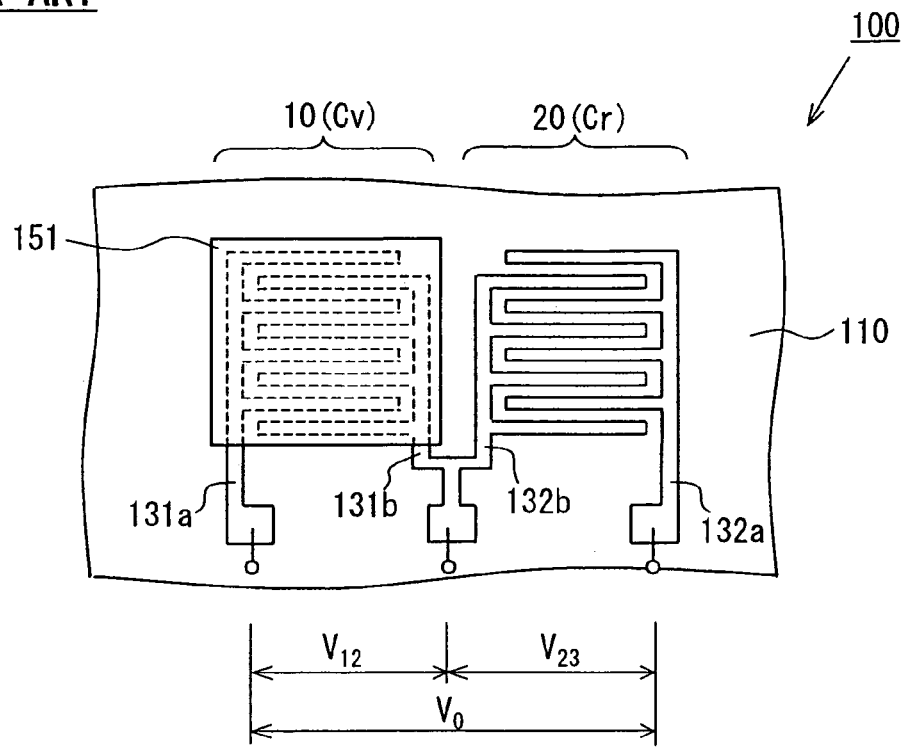
FIG. 8A is a plan view showing a conventional capacitive humidity sensor.
Figure 8B:
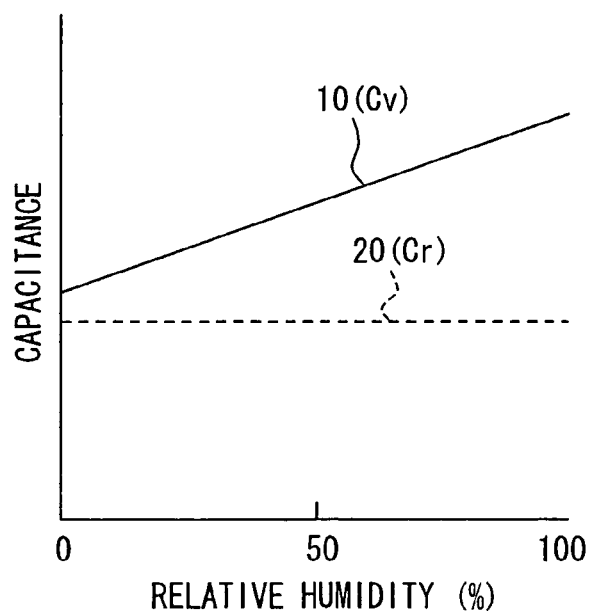
FIG. 8B is a graph showing a relationship between a relative humidity and capacitances in the conventional sensor.

As shown in FIG. 7B, detecting electrodes 131a, 131b are arranged so as to face each other in a substrate thickness direction through a clearance, and a first moisture-sensing film 151 is disposed in the clearance between the detecting electrodes 131a, 131b in a third embodiment. Similarly, reference electrodes 132a, 132b are arranged so as to face each other in a substrate thickness direction through a clearance, and a second moisture-sensing film 152 is disposed in the clearance between the detecting electrodes 132a, 132b. That is, the electrodes 131a, 131b (132a, 132b) have a parallel plate structure. The other parts in the third embodiment may be made similar to the first and second embodiments.

As shown in FIGS. 7A and 7B, a bottom electrode 131a is formed on a substrate 110 through an insulation film 120. A top electrode 131b is formed on the bottom electrode 131a through a protection film 140 and a first moisture-sensing film 151. Similarly, a bottom electrode 132a is formed on the substrate 110 through the insulation film 120. A top electrode 132b is formed on the bottom electrode 132a through the protection film 140 and a second moisture-sensing film 152. The top electrodes 131b, 132b are made of metal having a high humidity-resistance.

Further, a facing area between the detecting electrodes 131a, 131b is made larger than that between the reference electrodes 132a, 132b. A capacitor 170 having a predetermined capacitance is connected to the reference electrodes 132a, 132b in parallel.

According to the third embodiment, the second sensor element 162 of a reference portion 20 includes the second moisture-sensing film 152. Therefore, a temperature dependency in a sensor output can be reduced.

Further, because the second moisture-sensing film 152 is disposed on the bottom electrode 132a, the sensor 100 can be stably used in a high-temperature and high-humidity environment for a long time. Response performance can be kept better, and manufacturing cost can be kept low.

Furthermore, noises can be reduced, because a difference of the initial capacitances between the detecting portion 10 and the reference portion 20 can be reduced due to the capacitor 170.

In addition, the first and second moisture-sensing films 151, 152 in the sensor 100 having the parallel plate structure may be made of different materials, similarly to the second embodiment. Thus, the gradients of the capacitance variation to the humidity variation can be made different between the first and second sensor elements 161, 162. In this case, the facing area between the detecting electrodes 131a, 131b can be made approximately the same as that between the reference electrodes 132a, 132b. However, the facing areas may be made different from each other in this case.

Other Embodiments

In the above embodiments, the circuit 180 is integrated with the semiconductor substrate 110 together with the detecting portion 10 and the reference portion 20. Thus, a construction of the capacitive humidity sensor 100 can be simplified, and a size of the sensor 100 can be made smaller. However, the circuit 180 may be separately formed as a circuit substrate.

In the above embodiments, the semiconductor substrate 110 is made of silicon. Thereby, the semiconductor substrate 110 can be made with a general semiconductor-manufacturing technology in a low cost, and the semiconductor substrate 110 and the circuit 180 can be integrated into one chip. However, the substrate 110 may be made of other material, e.g., glass.

While the invention has been described with reference to a preferred embodiment thereof, it is to be understood that the invention is not limited to the preferred embodiment and constructions. The invention is intended to cover various modification and equivalent arrangements. The invention is intended to cover various combinations and configurations, which are preferred, other combinations and configurations, including more, less or only a single element, are also within the spirit and scope of the invention.

What is claimed is:

1. A capacitive humidity sensor comprising:
   a detecting portion including a first sensor element having a first moisture-sensing film, wherein a relative permittivity of the first moisture-sensing film varies in accordance with humidity such that a first capacitance of the first sensor element varies in accordance with the humidity; and
   a reference portion including
      a second sensor element having a second moisture-sensing film, wherein the second sensor element is connected to the first sensor element in series, and a relative permittivity of the second moisture-sensing film varies in accordance with the humidity such that a second capacitance of the second sensor element varies in accordance with the humidity, and
      a capacitor connected to the second sensor element in parallel, wherein a third capacitance of the capacitor is constant relative to a humidity variation, wherein
   the first sensor element has a first gradient of a first capacitance variation to the humidity variation, which is different from a second gradient of a second capacitance variation to the humidity variation in the second sensor element.

2. The capacitive humidity sensor according to claim 1, further comprising:
   a substrate, on which the first sensor element includes a first pair of electrodes facing each other through a first clearance, and on which the second sensor element includes a second pair of electrodes facing each other through a second clearance, wherein
   the first moisture-sensing film on the substrate covers the first pair of electrodes and the first clearance, and the second moisture-sensing film on the substrate covers the second pair of electrodes and the second clearance.

3. The capacitive humidity sensor according to claim 2, wherein:
   each of the first pair of electrodes has a shape of comb-teeth engaging with each other; and each of the second pair of electrodes has a shape of comb-teeth engaging with each other.

4. The capacitive humidity sensor according to claim 2, wherein:
each of the first pair of electrodes has a plurality of comb-teeth, and
a number of the comb-teeth of each of the first pair of electrodes is different from a number of comb-teeth of each of the second pair of electrodes.

5. The capacitive humidity sensor according to claim 4, wherein:
the first and second moisture-sensing films are made of a same material.

6. The capacitive humidity sensor according to claim 2, wherein:
the first clearance of the first pair of electrodes in the first sensor element is different from the second clearance of the second pair of electrodes in the second sensor element.

7. The capacitive humidity sensor according to claim 6, wherein:
the first and second moisture-sensing films are made of a same material.

8. The capacitive humidity sensor according to claim 2, wherein:
the first pair of electrodes have a first facing length in an electrode longitudinal direction, which is different from a second facing length of the second pair of electrodes.

9. The capacitive humidity sensor according to claim 8, wherein:
the first and second moisture-sensing films are made of a same material.

10. The capacitive humidity sensor according to claim 2, wherein:
the first and second moisture-sensing films are made of different materials.

11. The capacitive humidity sensor according to claim 10, wherein:
the first pair of electrodes and the second pair of electrodes have approximately a same shape.

12. The capacitive humidity sensor according to claim 1, further comprising:
a substrate, wherein
the first sensor element includes a first pair of electrodes facing each other in a thickness direction of the substrate, and the first moisture-sensing film is disposed between the first pair of electrodes, and
the second sensor element includes a second pair of electrodes facing each other in the thickness direction of the substrate, and the second moisture-sensing film is disposed between the second pair of electrodes.

13. The capacitive humidity sensor according to claim 12, wherein:
the first pair of electrodes have a first facing area therebetween, which is different from a second facing area between the second pair of electrodes.

14. The capacitive humidity sensor according to claim 13, wherein:
the first and second moisture-sensing films are made of a same material.

15. The capacitive humidity sensor according to claim 12, wherein:
the first and second moisture-sensing films are made of different materials.

16. The capacitive humidity sensor according to claim 15, wherein:
the first pair of electrodes have a first facing area therebetween, which is approximately equal to a second facing area between the second pair of electrodes.

17. The capacitive humidity sensor according to claim 1, further comprising:
a substrate, on which the capacitor is disposed as an electrical component.

18. The capacitive humidity sensor according to claim 1, further comprising:
a substrate, on which the capacitor is disposed, and
the capacitor is disposed under at least one of the first sensor element and the second sensor element.

19. The capacitive humidity sensor according to claim 1, further comprising:
a substrate; and
a circuit for processing a signal output from the detecting portion and the reference portion, wherein
the circuit is disposed on the substrate.

20. The capacitive humidity sensor according to claim 5,
the first clearance of the first pair of electrodes is different from the second clearance of the second pair of electrodes; and
the first pair of electrodes have a first facing area therebetween, which is approximately equal to a second facing area between the second pair of electrodes.

* * * * *